(12) United States Patent
Pfaendler

(10) Patent No.: US 6,482,818 B2
(45) Date of Patent: Nov. 19, 2002

(54) C-2 S/O-AND S/N FORMALDEHYDE ACETAL DERIVATIVES OF CARBAPENEM-3-CARBOXYLIC ACIDS AND THEIR USE AS ANTIBIOTICS AND β-LACTAMASE INHIBITORS

(76) Inventor: Hans Rudolf Pfaendler, Schuler Strasse 26, Stockdorf, D-82131 (DE)

(*) Notice: Subject to any disclaimer, the term of this patent is extended or adjusted under 35 U.S.C. 154(b) by 0 days.

(21) Appl. No.: 09/770,536

(22) Filed: Jan. 25, 2001

(65) Prior Publication Data

US 2001/0031749 A1 Oct. 18, 2001

Related U.S. Application Data

(63) Continuation of application No. PCT/EP99/05295, filed on Jul. 23, 1999.

(30) Foreign Application Priority Data

Jul. 28, 1998 (EP) .............................. 98114067

(51) Int. Cl.[7] .................... C07D 477/20; A61K 31/407; A61K 31/496; A61P 31/04
(52) U.S. Cl. ..................... 514/210.1; 540/350
(58) Field of Search ....................... 540/350; 514/210.1

(56) References Cited

FOREIGN PATENT DOCUMENTS

| EP | 0 079 244 A | 5/1983 | ......... C07D/487/04 |
| EP | 0 168 707 A | 1/1986 | ......... C07D/487/04 |
| EP | 0 169 410 A | 1/1986 | ......... C07D/487/04 |
| EP | 0 481 511 A | 4/1992 | ......... C07D/477/00 |
| JP | 60-54387 | 3/1985 | ......... C07D/487/04 |

*Primary Examiner*—Mark L. Berch
*Assistant Examiner*—Kahsay Habte
(74) *Attorney, Agent, or Firm*—Darby & Darby

(57) ABSTRACT

The compounds of the general formula I

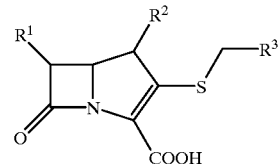

wherein $R^1$ denotes hydrogen, hydroxymethyl or 1-hydroxyethyl, $R^2$ denotes hydrogen or methyl and $R^3$ denotes a pharmaceutically acceptable group which is bonded to the remaining part of the molecule by an oxygen-carbon single bond or a nitrogen-carbon single bond, and their pharmaceutically acceptable salts, esters and amide derivatives are broad spectrum antibiotics and β-lactamase inhibitors.

8 Claims, No Drawings

C-2 S/O- AND S/N FORMALDEHYDE ACETAL DERIVATIVES OF CARBAPENEM-3-CARBOXYLIC ACIDS AND THEIR USE AS ANTIBIOTICS AND β-LACTAMASE INHIBITORS

This is a continuation of International Application Ser. No. PCT/EP99/05295, filed July 23, 1999, the entire disclosure of which is incorporated herein by reference.

DESCRIPTION AND BACKGROUND OF THE INVENTION

As to the relevant background prior art reference is made to EP 0 079 244 A, EP 0 168 707 A and EP 0 169 410 A. Herein compounds are described which are in part structurally close to certain compounds of the present invention. However, the compounds disclosed therein are either antibiotics having only β-lactamase activity or antibiotics having only bacterial activity.

This invention now relates to novel 2-S/O— and S/N formaldehyde acetal derivatives of carbapenem-3-carboxylic acids of the general formula I

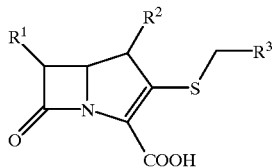

I wherein $R^1$ denotes hydrogen, hydroxymethyl or 1-hydroxyethyl, $R^2$ denotes hydrogen or methyl and $R^3$ denotes a pharmaceutically acceptable group which is bonded to the remaining part of the molecule by an oxygen-carbon single bond or a nitrogen-carbon single bond and which is selected from the group comprising substituted or unsubstituted: alkoxy, alkenyloxy, alkinyloxy, cycloalkoxy, N-heterocyclyl, heterocyclyloxy, heterocyclylcarbonyloxy, heterocyclylthiocarbonyloxy, acyloxy, thioacyloxy, alkoxycarbonyloxy, carbamoyloxy, thiocarbamoyloxy, heterocyclyloxycarbonyloxy, heterocyclyloxythiocarbonyloxy, N-heterocyclycarbamoyloxy, N-heterocyclylthiocarbamoyloxy, heterocyclylcarbonylamino, heterocyclylthiocarbonylamino, heterocyclyloxycarbonylamino, acylamino, alkoxycarbonylamino, alkoxythiocarbonylamino, thioacyclamino, N-heterocyclylcarbamoylamino, N-heterocyclylthiocarbamoylamino, carbamoylamino, thiocarbamoylaymino, imidoylamino, guanidino, N-heterocyclyl-alkoxycarbonylamino, N-heterocyclyl-alkylthiocarbonylamino and N-sulfonylamino where the foregoing alkyl, alkenyl, alkinyl, acyl, thioacyl or imidoyl molecule parts contain 1 to 6 carbon atoms and the heterocyclyl moiety is monocyclic or bicyclic and contains 3 to 10 ring atoms, of which one or more are selected from the series comprising: oxygen, sulphur and nitrogen and where the substituents of the above-mentioned groups R may be: alkyl, acyl, thioacyl, heterocyclyl, hydroxyl, hydroxyalkyl, alkoxy, hydroxyalkoxy, aminoalkoxy, amidinoalkoxy, guanidinoalkoxy, acyloxy, heterocyclyloxy, alkylheterocyclyloxy, hydroxyalkylheterocyclyloxy, aminoalkylheterocyclyloxy, carbamoyl, alkylcarbamoyl, dialkylcarbamoyl, carbamoyloxy, alkylcarbamoyloxy, dialkylcarbamoyloxy, thiocarbamoyl, alkylthiocarbamoyl, dialkylthiocarbamoyl, thiocarbamoyloxy, alkylthiocarbamoyloxy, dialkylthiocarbamoyloxy, mercapto, alkylthio, hydroxyalkylthio, aminoalkylthio, monoalkylaminoalkylthio, dialkylaminoalkylthio, amidinoalkylthio, acylthio, heterocyclylthio, alkylheterocyclylthio, hydroxyalkylheterocyclylthio, aminoalkylheterocyclylthio, carbamoylthio, monoalkylcarbamoylthio, dialkylcarbamoylthio, thiocarbamoylthio, alkylthiocarbamoylthio, dialkylcarbamoylthio, amino, monoalkylamino, hydroxyalkylamino, aminoalkylamino, dialkylamino, oxo, oximino, or alkylimino, imidoylamino, alkylimidoylamino, dialkylimidoylamino, trialkylammonium, cycloalkylamino, heterocyclylamino, alkylheterocyclylamino, heterocyclylcarbonylamino, alkylheterocyclylcarbonylamino, acylamino, amidino, monoalkylamidino, dialkylamidino, guanidino, alkylguanidino, dialkylguanidino, carbamoylamino, thiocarbamoylamino, alkylcarbamoylamino, thiocarbamoylamino, alkylthiocarbamoylamino, nitro, chloro, bromo, fluoro, iodo, azido, cyano, alkylsulphinyl, alkylsulphonyl, sulphonamido, sulphamoyloxy, alkylsulphamoyloxy, alkylsulphonyloxy or sulpho, sulphoxy, carboxamido, N-monoalkylcarboxamido, N,N-dialkylcarboxamido or carboxy, where the substituents, independently of one another, occur once or several times and their alkyl moiety contains 1 to 6 carbon atoms, and where the heterocyclic moiety is monocyclic or bicyclic and contains 3 to 10 ring atoms, of which one or more are selected from the series comprising: oxygen, sulphur and nitrogen, which compounds and their pharmaceutically acceptable salts, esters and amide derivatives are useful as antibiotics and as β-lactamase inhibitors.

Pharmaceutically acceptable groups $R^3$, which are bonded via an oxygen-carbon single bond or a nitrogen-carbon single bond are groups as are customary, for example, in the field β-lactam antibiotics or β-lactamase inhibitors. Such groups are found, for example, in M. S. Sassiver, A. Lewis in "Advances in Applied Microbiology", Ed. D. Perlman, Academic Press N.Y. (1970) or in many patents, e. g. U.S. Pat. No. 5,096,899.

The term "pharmaceutically acceptable salt" as used herein and in the claims, includes non-toxic acid and base salts and the salts of zwitterionic species. Salts with a base include inorganic salts such as sodium, potassium, magnesium and calcium, or ammonium and salts with non-toxic amines such as trialkylamines, alkanolamines, arginine or cyclic amines such as piperazine, procaine and other amines, which have been used to form salts of carboxylic acids. Salts with an acid include inorganic acid salts such as hydrochloride, sulfate, phosphate and the like and organic acid salts such as acetate, maleate, citrate, succinate, ascorbate, lactate, fumarate, tartrate and oxalate and other organic salts with acids which have been used to form salts with amines.

The pharmaceutically acceptable esters and amide derivatives as used herein, serve as prodrugs by being hydrolyzed in the body to yield the antibiotic per se. They are preferably administered orally since hydrolysis occurs principally under the influence of the digestive enzymes. Parenteral administration may be used in some instances where hydrolysis occurs in the blood. Examples of pharmaceutically acceptable esters and amide derivatives include physiologically hydrolyzable esters and amides known and used in the penicillin and cephalosporin fields as, e. g. in Advances in Drug Res. 17, 197 (1988). Such esters and amide derivatives are prepared by conventional techniques known in the art.

The compounds according to the invention have several asymmetric centers and can thus exist in in several stereochemical forms. The invention includes the mixture of isomers and the individual stereoisomers. The most preferred compounds of formula I have the 1R, 5S and 6S configuration of the substituted carbapenem nucleus and the 1'R or the 1'S configuration of the 6-(1-hydroxyethyl) side chain.

Additionally, asymmetric carbon atoms can be included in the substituent $R^3$. The invention includes the compounds having the R and S configuration in the substituent $R^3$.

This invention also relates to processes for the preparation of compounds (I), pharmaceutical compositions comprising such compounds and to methods of treatment comprising administering such compounds and compositions when an antibiotic effect is indicated.

The terminology for compounds of this class may either be based upon the root name "carbapenem" which employs a trivial and simple system of nomenclature (used in the general description). Alternatively, these compounds can also be described by the nomenclature according to the Chemical Abstract system (bicyclo-nomenclature) which is more appropriate to describe individual compounds of this family. Therefore the Chemical Abstract nomenclature is used within the Example Section.

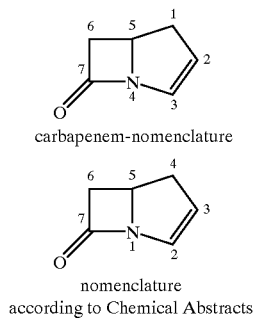

carbapenem-nomenclature nomenclature according to Chemical Abstracts

The classical β-lactam antibiotics such as the penicillins or the cephalosporins have partly become ineffective in the therapy of infectious diseases because of bacterial resistance. Besides the natural resistance of certain bacteria, many strains of pathogenic microorganisms have acquired resistance with continuous use of antibiotics on a large scale.

Thus, most species of Staphylococcus aureus have become resistant against the penicillins and many Gram-negative bacteria such as *Enterobacter cloacae, Pseudomonas aeruginosa* or even *Escherichia coli* have acquired resistance against the cephalosporins.

Consequently, there is a continuing need for new antibiotics. This search is particularly acute for antibiotics which have a wide spectrum or are orally active.

Within the β-lactams, the carbapenems represent the most effective class of compounds. These are active also against most penicillin- and cephalosporin resistant strains. However, the carbapenems currently used, are administered parenterally because they do not have sufficient oral activity. The lack of oral activity is known in the art and decribed, e. g in Infection 14, (1986), suppl. 2, S 115.

It is an objective of the present invention to provide a novel class of carbapenem antibiotics having a very broad antibacterial spectrum and being orally active.

The compounds of the above formula I are conveniently prepared in accordance with the following equation:

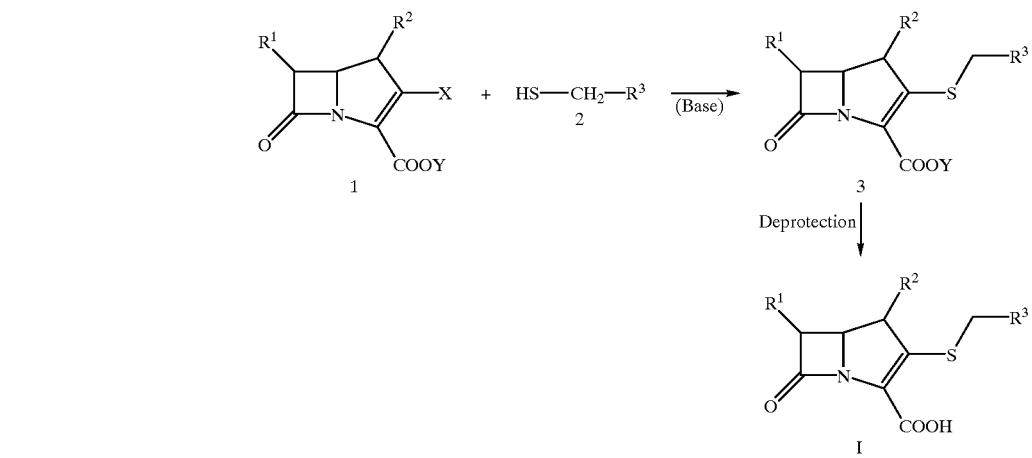

Thus, the intermediate 3 is prepared by reaction of the starting material 1, containing a leaving group X, wherein $R^1$ and $R^2$ are defined as above-mentioned, with a HS/O- or a HS/N-formaldehyde acetal HS—$CH_2$—$R^3$, preferably in presence of a base, wherein $R^3$ is defined as above-mentioned.

Because of the high reactivity of the HS/O- or HS/N-formaldehyde acetals, especially in presence of a base, the leaving group of X is not very critical. In fact, the reaction can be carried out by using a great variety of leaving groups X. Examples for such leaving groups X are alkoxy groups such as methoxy, alkylsulfonyloxy or arylsulfonyloxy groups such as methylsulfonyloxy, trifluormethylsulfonyloxy and p-toluenesulfonyloxy or dialkoxyphosphinoyloxy or or diaryloxyphosphinoyloxy groups such as dimethoxyphosphinoyloxy or preferably diphenoxylphosphinoyloxy.

Examples for the preparation of starting materials 1 are described in Heterocycles 1984, 21, 29–40, or in Tetrahedron Lett. 1980, 21, 4221–4224.

Inorganic or organic bases can be used in the process 1→3, for example potassium or caesium carbonate or tertiary amines such as triethylamine and pyridine or preferably hindered bases such as diisopropylethylamine and 2,6-dimethylpyridine. Because of the high reactivity of the above-mentioned HS/O- or HS/N-formaldehyde acetals the reaction temperature can be varied within a large range. Preferably the process 1→43 is carried out between −70° C and room temperature. A unpolar or polar solvent such as methylene chloride or acetonitrile, or preferably N,N-dimethylformamide, is suitable. The process 1→3 can also be carried out using phase transfer conditions, for example those using water, an unpolar solvent such as carbon tetrachloride or methylene chloride and a phase transfer catalyst such as tetrabutylammonium bromide.

The process 1→3 can also be carried out by using a preformed salt, preferably an alkali, earth alkali or tetraalkylammonium salt of the HS/O- or HS/N- formaldehyde acetals 2. With the inorganic salts, the process 1→3 is preferably carried out without additional base in a polar solvent, for example N,N-dimethylformamide. With the more soluble tetraalkylammonium salts, a less polar solvent such as tetrahydrofuran is preferable.

The protecting groups Y in the starting material 1 and in the intermediate 3 are easily removable radicals which are known per se, as are usually used for the purpose in organic synthesis. Protecting groups of this type are found, for example in Gunda I. Georg "The Organic Chemistry of β-Lactams", VCH Publishers UK, Cambridge, 1993, pp. 23–29.

Within the deprotection process 3→1, the free carboxylic acid or the corresponding inorganic salts are generated. In special cases it is possible that a selected substituent $R^3$ can be altered simultaneously during the process 3→1.

An example for such special processes is the simultaneous reduction of a 2- azidoethoxy group $R^3$ to a 2-aminoethoxy group during the deprotection of 3 (Y=p-nitrobenzyl) by a catalytic hydrogenolysis.

A prerequisite for the preparation of the compounds of structural formula I was the availability of the corresponding HS/O- and HS/N-formaldehyde acetals 2. We found that the classes of simple HS/O formaldehyde acetals ($R^3$= unsubstituted alkoxy) and HS/N-formaldehyde acetals ($R^3$= unsubstituted acylamino), were not known by prior art. Therefore it was also an object of the present invention to prepare the suitable novel formaldehyde derivatives 2.

2-Alkoxyalkylthiocarbapenems have been reported in EP 0 010 317. They were prepared from known unsubstituted 2-alkoxyalkanethiols as reagents. However, the 2- alkoxymethylthiocarbapenems were not accessible by this method since the required reagents, the HS/O formaldehyde acetals (2, $R^3$ =unsubstituted alkoxy) having 1 to 6 carbon atoms in their alkoxy molecular part, was a class of compounds, unknown by prior art. This class of reagents was considered to be too unstable to be of practical value (Houben-Weyl, Methoden der Org. Chemie., Vol. E 14a/1, G. Thieme ed., Stuttgart, N.Y. 1991, p. 793. This report constitutes a prejudice against the above-mentioned 2-alkoxymethanethiols and against the inventive solution leading to 2-alkoxymethylthiocarbapenem-3-carboxylic acids.

Although a compound with b.p. 52° C./20 mbar (15 mm) has been erroneously reported as methoxymethanethiol in the early literature (Chem. Zentralbl. 1912, 1192) we found no later reports of any use of this reagent in Chem. Abstr. Methoxymethanethiol was not accessible using the reported procedure, but had to be prepared on an entirely different (4→6→2 or 5→6→2) route. In fact, true methoxymethanethiol is by far more volatile than the reported compound and has a b.p. of 51° C. at ambient pressure! As the corresponding HS/O formaldehyde acetals were not accessible, 2- alkoxymethylthiocarbapenems I ($R^3$ methoxy) were never prepared and therefore not described in Chem. Abstr.

Similarly, the unsubstituted HS/N formaldehyde acetals 2 ($R^3$=unsubstituted acylamino) represented an unknown class of compounds. As reagents 2 ($R^3$=acylamino) are required in the preparation of acylaminomethylthiocarbapenems I ($R^3$= acylamino), the latter were not accessible by prior art either. Consequently, 2- acylaminomethylthiocarbapenems have not been described in Chem. Abstr.

The novel HSIO- or HS/N- formaldehyde acetals 2 are conveniently prepared via the following routes:

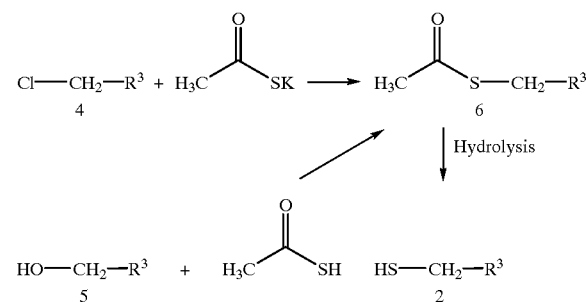

wherein $R^3$ is described as above-mentioned. The starting compounds 4 and 5 are known and can be prepared according to procedures known per se or are commercially available, as for example in the case of chloromethyl methyl ether (4, $R^3$=OCH$_3$) or N-hydroxymethylacetamide (5, $R^3$=HN—CO—CH$_3$). The process 4→6 is preferably carried out in a polar or unpolar solvent such as acetonitrile, ether or chloroform at −70° C. to room temperature, the process 5→6 can also be carried out in a solvent, or preferably, without a solvent (using an excess of thioacetic acid) at −30° C. to +60° C. Alternatively, instead of commercially available potassium thioacetate, other alkali or earth alkali thioacetates can be used.

The hydrolysis process 6→2 can be carried out using alkaline or acidic conditions, for example using alkali or earth alkali hydroxides or alkali or earth alkali alkoxides, preferably sodium hydroxide or sodium methoxide in a polar solvent such as water, acetonitrile or methyl alcohol. Suitable acidic conditions in the process 6→2 use strong acids, preferably hydrogen chloride, in a polar solvent such as water or methyl alcohol. The hydrolyses are preferably carried out at −30° C. to room temperature. The HS/O- or HS/N formaldehyde acetals 2 can be isolated in their free state or as alkali, earth alkali or tetraalkylammonium salts.

As already mentioned, currently used carbapenems do not possess sufficient oral activity. The oral activity of the compounds 1, according to the invention, arises from the novel S/O or S/N formaldehyde acetal groups. Similar derivatives of formaldehyde, i.e. an O/O formaldehyde acetal led to increased oral absorbability with the penicillins, for example with pivaloyloxymethyl esters of penicillins as described in Merck Index, 11th ed. 7484, p. 1193. The strong influence of spacer length of substituents was reported in the field of cephalosporins (Journ. Antibiot. 1993, 46, 177), where oral bioavailability has become a target of intensive research. In this literature report, a S/S formaldehyde acetal derivative was found to be superior over fourteen other compounds. Unfortunately, because of the unpolar character of the S/S acetal moiety, the activity against Pseudomonas aeruginosa, inherent in the class of aminothiazol cephalosporins, was largely reduced.

In the field of carbapenems, oral activity was also reported with 2-S/S formaldehyde acetal derivatives in Eur Pat. Appl. 0 481 511 A2, illustrating that the methylene group is suitable as a spacer between two sulfur atoms, to provide oral activity within this family of antibiotics.

However, no reports about S/O- or N/O formaldehyde acetals have appeared and no data about their oral bioavailability or their antibacterial activity have become known. Compared to the above-mentioned, reported 2-S/S-formaldehyde acetals, the compounds I, according to the invention, are more polar and therefore also active against the clinically important pathogen Pseudomonas aeruginosa.

Compared to other reported 2-alkoxyalkylthiocarbapenems, or 2-acylaminoalkylthiocarbapenems, having larger spacer lengths of their alkylene moiety, the compounds I are strongly preferred because of their oral absorbability.

In the general description of the present invention, the group $R^1$ denotes hydrogen, hydroxymethyl or 1-hydroxyethyl, $R^2$ denotes hydrogen or methyl and $R^3$ denotes a pharmaceutically acceptable group, which is bonded to the remaining part of the molecule by an oxygen-carbon single bond or a nitrogen-carbon single bond and which is selected from the group comprising substituted or unsubstituted: alkoxy, alkenyloxy, alkinyloxy, cycloalkoxy, N-heterocyclyl, heterocyclyloxy, heterocyclylcarbonyloxy, heterocyclylthiocarbonyloxy, acyloxy, thioacyloxy, alkoxycarbonyloxy, carbamoyloxy, thiocarbamoyloxy, heterocyclyloxycarbonyloxy, heterocyclyloxythiocarbonyloxy, N-heterocyclycarbamoyloxy, N-heterocyclylthiocarbamoyloxy, heterocyclylcarbonylamino, heterocyclylthiocarbonylamino, heterocyclyloxycarbonylamino, acyclamino, alkoxycarbonylamino, alkoxythiocarbonylamino, thioacylamino, N-heterocyclylcarbamoylamino, N-heterocyclylthiocarbamoylamino, carbamoylamino, thiocarbamoylamino, imidoylamino, guanidino, N-heterocyclyl-alkoxycarbonylamino, N-heterocyclyl-alkylthiocarbonylamino and N-sulfonylamino where the foregoing alkyl, alkenyl, alkinyl, acyl, thioacyl or imidoyl molecule parts contain 1 to 6 carbon atoms and the heterocyclyl moiety is monocyclic or bicyclic and contains 3 to 10 ring atoms, of which one or more are selected from the series comprising: oxygen, sulphur and nitrogen and where the substituents of the above-mentioned groups R may be: alkyl, acyl, thioacyl, heterocyclyl, hydroxyl, hydroxyalkyl, alkoxy, hydroxyalkoxy, aminoalkoxy, amidinoalkoxy, guanidinoalkoxy, acyloxy, heterocyclyloxy, alkylheterocyclyloxy, hydroxyalkylheterocyclyloxy, aminoalkylheterocyclyloxy, carbamoyl, alkylcarbamoyl, dialkylcarbamoyl, carbamoyloxy, alkylcarbamoyloxy, dialkylcarbamoyloxy,thiocarbamoyl, alkylthiocarbamoyl, dialkylthiocarbamoyl, thiocarbamoyloxy, alkylthiocarbamoyloxy, dialkylthiocarbamoyloxy, mercapto, alkylthio, hydroxyalkylthio, aminoalkylthio, monoalkylaminoalkylthio, dialkylaminoalkylthio, amidinoalkylthio, acylthio, heterocyclylthio, alkylheterocyclylthio, hydroxyalkylheterocyclylthio, aminoalkylheterocyclylthio, carbamoylthio, monoalkylcarbamoylthio, dialkylcarbamoylthio, thiocarbamoylthio, alkylthiocarbamoylthio, dialkylcarbamoylthio, amino, monoalkylamino, hydroxyalkylamino, aminoalkylamino, dialkylamino, oxo, oximino, or alkylimino, imidoylamino, alkylimidoylamino, dialkylimidoylamino, tetraalkylammonium, cycloalkylamino, heterocyclylamino, alkylheterocyclylamino, heterocyclylcarbonylamino, alkylheterocyclylcarbonylamino, acylamino, amidino, monoalkylamidino, dialkylamidino, guanidino, alkylguanidino, dialkylguanidino, carbamoylamino, thiocarbamoylamino, alkylcarbamoylamino, thiocarbamoylamino, alkylthiocarbamoylamino, nitro, chlorine, bromine, fluorine, iodine, azido, cyano, alkylsulphinyl, alkylsulphonyl, sulphonamido, sulphamoyloxy, alkylsulphamoyloxy, alkylsulphonyloxy or sulpho, sulphoxy, carboxamido, N-monoalkylcarboxamido, N,N-dialkylcarboxamido or carboxy, where the substituents, independently of one another, occur once or several times and their alkyl moiety contains 1 to 6 carbon atoms, and where the heterocyclic moiety is monocyclic or bicyclic and contains 3 to 10 ring atoms, of which one or more are selected from the series comprising: oxygen, sulphur and nitrogen.

A preferred class of compounds I is that, in which R1 denotes hydrogen, hydroxymethyl or 1-hydroxyethyl, $R^2$ denotes hydrogen or methyl and $R^3$ denotes substituted or unsubstituted alkoxy, heterocyclyloxy, acyloxy, carbamoyloxy, N-heterocyclyl, acylamino, carbamoylamino, imidoylamino where the foregoing alkyl, acyl, thioacyl, or imidoyl molecule parts contain 1 to 3 carbon atoms and the heterocyclyl moiety is monocyclic and contains 3 to 6 ring atoms, of which one or more are selected from the series comprising : oxygen, sulphur and nitrogen and where the substituents of the above-mentioned groups R may be: alkyl, acyl, thioacyl, heterocyclyl, hydroxyl, hydroxyalkyl, alkoxy, hydroxyalkoxy, aminoalkoxy, amidinoalkoxy, guanidinoalkoxy, acyloxy, heterocyclyloxy, alkylheterocyclyloxy, hydroxyalkylheterocyclyloxy, aminoalkylheterocyclyloxy, carbamoyl, alkylcarbamoyl, dialkylcarbamoyl, carbamoyloxy, alkylcarbamoyloxy, dialkylcarbamoyloxy, thiocarbamoyl, alkylthiocarbamoyl, dialkylthiocarbamoyl thiocarbamoyloxy, alkylthiocarbamoyloxy, dialkylthiocarbamoyloxy, mercapto, alkylthio, hydroxyalkylthio, aminoalkylthio, monoalkylaminoalkylthio, dialkylaminoalkylthio, amidinoalkylthio, acylthio, heterocyclylthio, alkylheterocyclylthio, hydroxyalkylheterocyclylthio, aminoalkylheterocyclylthio, carbamoylthio, monoalkylcarbamoylthio, dialkylcarbamoylthio, thiocarbamoylthio, alkylthiocarbamoylthio, dialkylcarbamoylthio, amino, monoalkylamino, hydroxyalkylamino, aminoalkylamino, dialkylamino, oxo, oximino, or alkylimino, imidoylamino, alkylimidoylamino, dialkylimidoylamino, tetraalkylammonium, cycloalkylamino, heterocyclylamino, alkylheterocyclylamino, heterocyclylcarbonylamino, alkylheterocyclylcarbonylamino, acylamino, amidino, monoalkylamidino, dialkylamidino, guanidino, alkylguanidino, dialkylguanidino, carbamoylamino, thiocarbamoylamino, alkylcarbamoylamino, thiocarbamoylamino, alkylthiocarbamoylamino, nitro, chlorine, bromine, fluorine, iodine, azido, cyano, alkylsulphinyl, alkylsulphonyl, sulphonamido, sulphamoyloxy, alkylsulphamoyloxy, alkylsulphonyloxy or sulpho, sulphoxy, carboxamido, N-monoalkylcarboxamido, N,N-dialkylcarboxamido or carboxy, where the substituents, independently of one another, occur once or several times and their alkyl moiety contains 1 to 6 carbon atoms, and where the heterocyclic moiety is monocyclic and contains 3 to 6ring atoms, of which one or more are selected from the series comprising: oxygen, sulphur and nitrogen.

An especially preferred class of compounds I, according to the invention, is the one, in which $R^1$ denotes 1-hydoxyethyl, $R^2$ denotes methyl and $R^3$ denotes substituted alkoxy, acylamino, alkylcarbamoylamino, alkoxycarbamoylamino, N-heterocyclyl and imidoylamino, where the foregoing alkyl, acyl or imidoyl molecule parts contain 1 to 3 carbon atoms and the heterocyclyl moiety is monocyclic and contains 3 to 6 ring atoms, of which one or more are selected from the series comprising: oxygen, sulphur and nitrogen and where the substituents of the above-mentioned groups $R^3$ are basic groups such as amino, alkylamino, dialkylamino, imidoyl, amidino and guanidino. In this case the compounds I according to the invention are very polar and can exist in their zwitterionic form. Therefore such compounds are especially active against Gram-negative bacteria including Pseudomonas aeruginosa.

A selection of compounds I according to the invention showed high antibacterial acivity in the disc susceptibility test after application of 10 micrograms with the following inhibition diameters: Staph. aureus (9–39 mm), E. coli (27–34 mm), E. cloacae (23–27 mm) and Ps. aeruginosa (13–26 mm). These data correspond to those of a clinically useful injectable carbapenem as described in Journ. Antimicrob. Chemotherapy 24, (1989), Suppl. A, 253.

Therefore these new antibiotics are active against a range of bacterial pathogens, which representatively include both gram-positive and gram-negative bacteria such as *Staphylococcus aureus, Escherichia coli, Enterobacter cloacae* Enterococcus and *Pseudomonas aeruginosa*.

Surprisingly, we found that the compounds according to the invention strongly inhibited bacterial β-lactamases isolated from *Enterobacter cloacae* and *Escherichia coli*. Moreover, all tested ceftazidime resistant Gram-negative pathogens became susceptible to a combination of ceftazidime and the compounds according to the invention. Thus, these compounds are also very potent β-lactamase inhibitors. The very high activity as β-lactamase inhibitors of the compounds I according to the invention was also observed with isolated bacterial enzymes in the nitrocefin test (R. Reimer, Methodicum Chimicum: Antibiotics, Vitamins and Hormons; F. Korte, M. Goto, eds., Thieme, Stuttgart, 1977, p.11, E. Wasielewski, Arzneimittel, Vol. 4; Chemotherapeutica, Part 1, Verlag Chemie, Weinheim 1972).

A representative of the compounds I according to the invention showed high blood levels in mice after oral treatment with 25 mg per kg, showing the oral absorbability.

Therefore the present invention has the objective of providing a new class of carbapenem antibiotics and β-lactamase inhibitors, which is important in veterinary and human therapy and in inanimate systems. The high and broad spectrum antibacterial activity and β-lactamase inhibition potency of the compounds according to the invention, in combination with their oral activity, could not be expected to this extent from the prior art.

The new compounds according to the invention are valuable antimicrobial substances which are active against most Gram-positive and Gram-negative pathogens including also most penicillin- and cephalosporin resistant and anaerobic bacteria. The free acid and in particular the alkaline and earth metal salts or the zwitterionic species are useful bactericides and can be empolyed to remove pathogens from dental and medical equipment for removing microorganisms and for therapeutic use in humans and animals. For this latter purpose, pharmaceutically acceptable salts as are known per se and are used in the administration of penicillins and cephalosporins, are used. These salts can be used together with pharmaceutically acceptable liquid and solid excipients to form suitable dose unit forms such as pills, tablets, capsules, suppositories, syrups, elixirs and the like, which can be prepared by processes which are known per se.

The new compounds are valuable antibiotics against most pathogenic bacteria and, accordingly, are used in human and veterinary medicine. They can be used as antibacterial medicaments for treating infections caused by Gram-positive and Gram-negative bacteria, for example by *Staphylococcus aureus, Escherichia coli, Klebsiella pneumoniae, Bacillus subtilis, Salmonella typhosa, Enterobacter cloacae,* Enterococcus, *Pseudomonas aeruginosa* and *Bacterium proteus*.

The antibacterial agents can furthermore be used as additives for animal feeds, for preserving foodstuffs or feeds and as desinfectants. For example, they can be used in aqueous preparations in concentrations in the range 0.1 to 100 parts of antibiotic/million parts of solution for destroying and inhibiting the growth of harmful bacteria on medical equipment and as bactericides in industrial applications, for example in water-based paints and in soft water for paper mills, for inhibiting the growth of harmful bacteria.

The products according to the invention may be used alone or together with other active components in any of a large number of pharmaceutical preparations. These preparations can be used in capsule form or as tablets, powders or liquid solutions or as suspensions or elixirs. They can be administered orally, intravenously or intramuscularly.

The preparations are preferably administered in a form which is suitable for absorption through the gastrointestinal tract. Tablets and capsules for oral administration may be in dose unit form and can contain customary medicament excipients, such as binders, for example syrup, gum arabic, gelatin, sorbitol or polyvinylpyrrolidone, fillers, for example lactose, sugar, maize starch, calcium phosphate, sorbitol or glycine, lubricants, for example magnesium stearate, talc, polyethylene glycol or silica, disintegrants for example potato starch, or acceptable wetting agents such as sodium lauryl sulfate. The tablets may be coated by processes which are known per se. Oral liquid preparations can be in the form of of aqueous or oily suspensions, solutions, emulsions, syrups, elixirs and the like or can exist as dry product, for example for reconstitution before using water or other suitable excipients. Liquid preparations of this type can contain additives which are known per se, such as suspending agents, for example sorbitol syrup, methylcellulose, glucose/sugar syrup, gelatin, hydroxyethylcellulose, carboxymethylcellulose, aluminum stearate gel, or hydrogenated edible oils, for example almond oil, fractionated coconut oil, oily esters, propylene glycol or ethyl alcohol, preservatives, for example methyl or propyl p-hydroxybenzoate or sorbic acid. Suppositories contain suppository bases which are known per se, for example cocoa butter or other glycerides.

The preparations for injection can be in dose unit form in ampoules or in containers containing several doses along with an added preservative. The preparations can be in the form of suspensions, solutions or emulsions in oily or aqueous excipients, and they may contain formulation agents such as suspending agents, stabilizers and/or dispersants. Alternatively, the active component may be in powder form for reconstitution before using a suitable excipient, for example sterile, pyrogen-free water.

The preparations can also be in suitable form for absorption through the muscous membranes of the nose and of the throat or of the bronchial tissue, and can be in the form of powders or liquid sprays or inhalants, sucking sweets, as throat paints, etc. For eye and ear medications, the preparations can be used in the form of individual capsules in liquid or semi-solid form or they can be used as drops, etc. Topical applications can exist or be formulated in hydrophobic vehicles as ointments, creams, lotions, paints, powders, etc.

The preparations according to the invention can contain, in addition to the excipient, other components such as stabilizers, binders, antioxidants, preservatives, lubricants, suspending agents, viscosity control agents or flavours or the like.

The preparations according to the invention may also contain, in addition to the excipient, enzyme inhibitors, e.g. cilastatin (Merck Index, 11th ed. 2275) to increase the therapeutic effect.

In addition, the preparations may contain one or more active antibacterial components to obtain a broader antibiotic range. Examples for such other active components are antibiotics, preferably β-lactam antibiotics, e.g. penicillins such as Ampicillin or Amoxycillin or cephalosporins such as Cephalexin, Cefachlor or Ceftazidime. With such added conventional β-lactam antibiotics, the active component according to the invention, acts as an antibacterial and as an inhibitor of bacterial β-lactamases.

For veterinary medicine, the preparations can be formulated, for example, as an intramammary preparation in either long-acting or rapid-release vehicles. The dose to be administered is highly dependent on the state of the subject to be treated and the weight of the host, and on the method and frequency of administration. In general, a daily oral dose contains about 10 to about 200 mg of active component/kg of body weight of the subject in case of one or more administrations per day. A preferred daily dose for adult humans is in the range of about 20 to 120 mg of active componentl/kg of body weight.

The preparations according to the invention can be administered in various unit dose forms, for example in solid or liquid dose forms which can be taken orally. The preparations can contain 0.1 to 99% of active material per unit dose, either in solid or in liquid form. The preferred range is about 10 to 60%. The preparations generally contain 15 to about 1500 mg of active component but it is generally preferred to use a dose amount in the range about 250 to 1000 mg. In the case of parenteral administration, the unit dose is normally the pure compound in a sterile water solution or in the form of a soluble powder, which may be dissolved.

The examples below illustrate the products, processes, preparations and methods of treatment according to the invention.

EXAMPLE 1

Methoxymethanethiol

To a 5.2 N aqueous solution of sodium hydroxide (7.7 ml, 40 mmol),at 0° C., with stirring, methoxymethyl thiolacetate (2.40 g, 20 mmol) was added. After 30 min, to the resulting yellow solution 5 N aqueous hydrogen chloride (4.0 ml, 20 mmol) was added, where upon an oily layer separated. After saturation of the aqueous layer with sodium chloride at 0° C., the oily phase was separated, dried with magnesium sulfate, filtered and the filtrate distilled at ambient pressure, yielding a colourless liquid, b.p. 51° C. NMR-spectrum in $CDCl_3$ 2.0 (t, 1H, J =12 Hz), 3.4 (s, 3H), 4.8 (d, 2H, J=12 Hz) ppm.

Alternatively, the two phase mixture was extracted with deuteriochloroform. The resulting solution was dried over magnesium sulfate, filtered and stored in a refrigerator. It contained pure title compound (1.17 g, 80%). This solution was exrtracted with 2 N aqueous sodium hydroxide (7.5 ml, 15 mmol) and the extract immediately lyophilized in high vacuo yielding colourless solid sodium methoxymethylthiolate.

EXAMPLE 2

2-(Azidoethyloxy)methanethiol

Into a mixture of 2-azidoethanol (2.0 g, 23 mmol) and trioxane (0.74 g, 8.2 mmol) dry hydrogen chloride was introduced at −10° C. After 1.5 hr, the solid liquidified. After flushing of the apparatus with nitrogen the mixture consisted of (2-azidoethyl) chloromethyl ether. NMR-spectrum in $CDCl_3$: 3.5 (m, 2H), 3.9 (m, 2H), 5.5 (s, 2H) ppm.

The (2-azidoethyl) chloromethyl ether (crude product, 23 mmol) was added at 0° C. to a stirred suspension of potassium thiolacetate (2.63 g, 23 mmol) in dry ether (7.5 ml).

The mixture was allowed to stir at room temperature overnight. Insoluble material was removed by filtration and the filtrate was evaporated in vacuo, leaving an orange liquid. It was distilled in high vacuum (0.003 mbar) (0.002 mm) using a short path distillation apparatus and a safety shield. Pure (2-azidoethoxy)methyl thiolacetate, b.p. 80–90° C./0.003 mbar (0.002 mm) was obtained as a pale yellow liquid in 65% yield. NMR-spectrum in $CDCl_3$: 2.38 (s, 3H), 3.36 (m, 2H), 3.61 (m, 2H), 5.10 (s, 2H) ppm.

To 0.20 N aqueous NaOH (121 ml, 24.2 mmol) at 0° C. a solution of (2-azidoethoxy)methyl thiolacetate (848 mg, 4.84 mmol) in tetrahydrofuran (5 ml) was added dropwise with stirring. The reaction mixture was allowed to stir for 15 min at 0° C. The resulting solution was washed with ether (100 ml) and then acidified at 0° C. with 1.0 N aqueous HCl (19.4 ml) to a pH of 6. The aqueous solution was then extracted twice with portions of ether (50 ml). The combined ether layers were dried over magnesium sulfate and solvent removed in vacuo (17 mbar) (13 mm).The resulting crude product was chromatographed on silica gel (200–63 μm, 23 g) using hexane-ether (9:1) to give colourless title compound in 47% yield after drying at 17 mbar (13 mm). NMR-spectrum in $CDCl_3$: 2.0 (t, 2H, =10 Hz), 3.4 (t, 2H, J=6 Hz), 3.7 (t, 2H, J=6 Hz), 4.8 (d, 2H, J=10 Hz) ppm.

EXAMPLE 3

(2-Azido-1,1-dimethylethoxy)methanethiol

To a stirred suspension of sodium hydride (310 mg, 13 mmol) in dry tetrahydrofuran (5 ml), at 0° C., a solution of 1-azido-2-methyl-2-propanol (1.15 g, 10 mmol) in dry THF (2 ml) was added. When hydrogen evolution had stopped, to the pale yellow solution dry hexamethylphosphorous triamide (3 ml) and chloromethyl methyl ether (1.14 ml, 15 mmol) were added at 0° C. and the reaction mixture stirred at room temperature overnight. The reaction mixture was poured on 10% aqueous NaCl solution (40 ml) and extracted twice with two portions (150 and 50 ml) of ether. The combined ether layers were washed twice with 10% NaCl (50 ml) and with saturated NaCl (50 ml). The ether layer was dried over magnesium sulfate and the solvent removed in vacuo (17 mbar) (13 mm) yielding formaldehyde ((2-azido-1,1-dimethylethyl) methyl acetal (1.41 g 89%).

NMR-spectrum in $CDCl_3$: 1.28 (s, 6H), 3.22 (s, 2H), 3.39 (s, 3H), 4.74 (s, 2H) ppm.

To a stirred solution of formaldehyde ((2-azido-1,1-dimethylethyl) methyl acetal (1.35 g, 8.47 mmol) in dry methylene chloride (5 ml) 1 M boron trichloride solution (3.64 ml, 3.64 mmol) was added at 0° C. The reaction mixture was stirred at room temperature for 3 hr to give a solution of (2-azido-1,1-dimethylethyl) chloromethyl ether. NMR-spectrum in $CDCl_3$: 1.36 (s, 6H), 3.24 (ABq, 2H), 5.60 (s, 2H) ppm.

To a suspension of powdered solid potassium thioacetate (1.28 g, 11.3 mmol) in dry methylene chloride (8 ml), at 0° C, the above-mentioned solution (8.0 ml) containing (2-azido-1,1-dimethylethyl) chloromethyl ether (1.23 g, 7.53), was added with stirring and the resulting suspension allowed to stir at room temperature overnight. The resulting mixture was diluted with methylene chloride (80 ml), washed tree times with port-ions (30 ml each) of water and once with saturated NaCl (30 ml). The organic layer was dried over magnesium sulfate and the solvent removed in vacuo (17 mbar) (13 mm) to give crude (2-azido-1,1-dimethylethoxy)methyl thiolacetate (1.30 g, 85%). It was purified by column chromatography on silica gel (40-60 µm) using hexane-ether (4:1) yielding pure (2-azido-1,1-dimethylethoxy)methyl thiolacetate (0.81 g, 53%) as a colour-less liquid. NMR-spectrum in $CDCl_3$: 1.28 (s, 6H), 2.37 (s, 3H), 3.21 (s, 2H), 5.02 (s, 2H).

To a stirred 0.1N solution of sodium hydroxide (25 ml, 2.5 mmol), at 0° C., (2-azido-1,1-dimethylethoxy)methyl thiolacetate (102 mg, 0.5 mmol), dissolved in THF (0.5 ml) was added. The reaction mixture was stirred at 0° C. for 90 min. The solution was washed with ether (15 ml) and then acidified at 0° C. with 1N HCl (1.8 ml, 1.8 mmol) to pH 6–7. The solution was stirred at 0° C. for 30 min and then transferred to a separatory funnel. After having shaken for 3 min, the organic layer was collected and the aqueous layer reextracted twice with portions (8 ml) of ether. The combined ether layers were dried over magnesium sulfate and the solvent removed in vacuo (17 mbar) (13 mm) yielding the title compound as a pale yellow liquid (67 mg, 83%). NMR-spectrum in $CDCl_3$: 1.28 (s, 6H), 2.18 (t, 1H, J=10 Hz), 3.23 (s, 2H), 4.73 (d, 2H, J=10 Hz) ppm.

EXAMPLE 4
N-(Mercaptomethyl)-acetamide

N-(Hydroxymethyl)-acetamide (13.4 g, 0.15 mol) and thiolacetic acid (14.3 g, 0.188 mol) were heated for 3 days at 40° C. The resulting mixture was chromatographed on silica gel (63–200 um, 700 g) with toluene-ethyl acetate 4:1 and 1:1 to give pure crystalline acetamidomethyl thiolacetate (14.2 g, 64%), m.p. 93–94° C.

Acetamidomethyl thiolacetate (1.47 g, 10 mmol) was dissolved in 2.0 N hydrogen chloride in dry methanol (1.8 ml) and the resulting solution kept at room temperature for 3.5 hr. It was neutralized (pH=7) with a 2 N solution of sodium methoxide in dry methanol (1.8 ml). Precipitated sodium chloride was removed by filtration and the filtrate evaporated in vacuo. The residue was chromatographed on silica gel (63–200 µm, 30 g) using ethyl acetate to give the pure title compound (0.70 g, 67%). It was kept at −30° C. under argon. NMR-spectrum in $CDCl_3$: 1.95 (s, 3H), 2.38 (t, 1H, J=9 Hz), 4.28 (dd, 2H, J=9 Hz) 6.81 (broad s, 1H) ppm.

EXAMPLE 5
2-Azido-N-(mercaptomethyl)-acetamide

A mixture of 2-azido-acetamide (1.40 g, 14 mmol), 30% aqueous (methanol free) formaldehyde (1.40 g, 14 mmol) and 1.0 N aqueous KOH (0.28 ml, 0.28 mmol) was stirred at 0° C for 4 hrs. To the reaction mixture 1.0 N aqueous HCl was added (pH=7) and the resulting mixture evaporated in vacuo. The residue was suspended in ethyl acetate (50 ml), the solution dried over magnesium sulfate, filtered and the filtrate concentrated to a volume of 5 ml. Chromatography on silica gel (63–200 µm, 18 g) with ethyl acetate afforded 2-azido-N-(hydroxymethyl)-acetamide as a colourless oil in 90% yield. NMR-spectrum in $CDCl_3$: 3.6 (broad signal, 1H), 4.0 (s, 2H), 4.8 (d, 2H, J=6 Hz), 7.3 (broad signal 1H) ppm.

To 2-azido-N-(hydroxymethyl)-acetamide (650 mg, 5 mmol) at −10° C. oxalyl chloride (635 mg, 5 mmol) was added. After 10 min gas evolution had ceased. The mixture was diluted in $CDCl_3$. NMR-Spectrum in $CDCl_3$: 4.1 (s, 2H), 5.2 (d, 2H, J=10 Hz), 7.3 (broad signal, 1H) ppm. The NMR was consitent with 2-azido-N-(chloromethyl)-acetamide (yield 75%).

To the solution of the crude 2-azido-N-(chloromethyl)-acetamide (715 mg) in $CDCl_3$ (4 ml) potassium thioacetate (520 mg, 4.6 mmol) was added at 0° C. and the suspension stirred at room temperature overnight. The mixture was diluted with chloroform (50 ml) and the solution subsequently washed twice with portions (15 ml) of water and with brine (10 ml). The organic layer was dried over magnesium sulfate and the solvent evaporated in vacuo leaving a noncrystalline solid (530 mg). It was chromatographed on silica gel (63–200 pm) using toluene-ethyl acetate (2:1) to give 400 mg (56%) of pure (2-azidoacetamido)methyl thiolacetate. NMR spectrum in $CDCl_3$: 2.4 (s, 3H), 4.0 (s, 2H), 4.7 (d, 2H, J=7 Hz), 7.2 (broad signal, 1H) ppm.

Pure (2-azidoacetamido)methyl thiolacetate (56 mg, 0.28 mmol) was dissolved in 1.8 N HCl in dry methanol (0.6 ml, 1.1 mmol) and the solution stirred at room temperature for 6 hrs. It was neutralized with 2.2 N sodium methoxide in dry methanol (0.46 ml, 1.03 mmol) (pH=6). The precipitated sodium chloride was removed by filtration and the filtrate diluted with DMF-$d_6$ (0.7 ml) and then methanol was removed in vacuo (15 mm) and finally in high vacuo (0.0013 mbar) (0.001 mm).

The DMF-$d_6$ solution was kept at −80° C. NMR spectroscopy showed the title compound (yield 56%, determined with 10 µl of benzene as internal standard). NMR spectrum in DMF-$d_6$: 2.9 (broad signal, 1H), 3.95 (s, 2H), 4.38 (dd, 2H), 8.9 (broad signal, 1H) ppm.

EXAMPLE 6
1-Ethyl-4-(mercaptomethyl)-piperazine-2,3-dione

To a solution of 1-ethylpiperazine-2,3-dione (2.13 g, 15 mmol) in 30% aqueous (methanol free) formaldehyde (15 mmol) potassium hydroxide (150 mg, 2.7 mmol) was added and the mixture stirred at 50° C. for 7 days. It was neutralized with 5 N aqueous hydrochloric acid (50 µl) to pH=7. The mixture was evaporated at 15 mm and then dried in high vacuo (0.0013 mbar) (0.001 mm) to give 1-ethyl-4-(hydroxymethyl)-piperazine-2,3-dione as a colourless solid (100%). NMR-spectrum in $CDCl_3$: 1.15 (broad signal, 1H), 1.15 (t, 3H, J=7 Hz), 3.47 (q, 2H, J=7 Hz), 3.54 (m, 2H), 3.68 (m, 2H), 4.88 (s, 2H) ppm.

To 1-ethyl-4-(hydroxymethyl)-piperazine-2,3-dione (156 mg, 0.906 mmol) oxalyl chloride (78 µl, 0.906 mmol) was added at −10° C. The mixture was stirred at −10° C. for 2 hrs. Gas evolution had ceased after 30 min. The reaction mixture was dried in high vacuo to give 1-(chloromethyl)-4-ethyl-piperazine-2,3-dione (100%). NMR-spectrum in $CDCl_3$: 1.15 (t, 3H, J=7 Hz), 3.42 (q, 2H, J=7 Hz), 3.65 (broad signal, 4H), 5.30 (s, 2H) ppm.

To a solution of crude 1-(chloromethyl)-4-ethyl-piperazine-2,3-dione (170 mg, 0.9 mmol) in $CDCl_3$ (1 ml) solid potassium thioacetate (123 mg, 1.08 mmol) was added with stirring at 0° C. The reaction mixxture was allowed to stir at room temperature overnight. The mixture was centifuged and the supernatant solution collected. The residual solid (KCl) was washed with $CDCl_3$ (2 ml) and the organic solutions combined and the solvent removed in vacuo. The residue was chromatographed on silica gel (6 g, 63–200 µm) using chloroform-methanol (19:1) to give 1-(acetylthiomethyl)-4- ethyl-piperazine-2,3-dione as a white solid (overall yield 44%). NMR-specrum in $CDCl_3$: 1.22 (t, 3H, J=7 Hz), 2.44 (s, 3H), 3.48 (q, 2H, J=7 Hz), 3.4–3.7 (m, 4H), 4.95 (s, 2H) ppm.

1-(Acetylthiomethyl)-4-ethyl-piperazine-2,4-dione (74 mg, 0.32 mmol) was dissolved in 1.95 N HCl in methanol (0.56 ml, 1.2 mmol) and the solution allowed to stir at room temperature for 6 hrs. The mixture was neutralized at 0° C. with 2.24 N sodium methoxide in dry methanol (0.54 ml, 1.2 mmol) to pH=6. Precipitated sodium chloride was removed by filtration and the filtrate evaporated in vacuo and the residue dried at 0.0013 mbar (0.001 mm). It was chromatographed on silica gel (2.0 g, 63–200 μm) using chloroform-methanol (19:1) to give the title compound as a colourless solid (yield 80%). NMR-spectrum in $CDCl_3$: 1.23 (t, 3H, J=7 Hz), 2.43 (broad signal, 1H) 3.55 (q, 2H, J=7Hz), 3.67 (broad s, 4H), 4.60 (broad s, 2H) ppm.

EXAMPLE 7

Sodium or potassium (4R,5S,6S)-6-((1'R)-hydroxyethyl)-3-(methoxymethylthio)-4- methyl-7-oxo-1-azabicyclo[3.2.0]hept-2-ene-2-carboxylate (Ia)

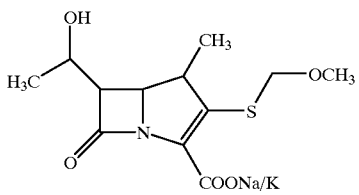

p-Nitrobenzyl (4R,5S,6S)-6-((1'R)-hydroxyethyl)-3-(methoxymethylthio)-4-methyl-7- oxo-1-azabicyclo[3.2.0]hept-2-ene-2-carboxylate

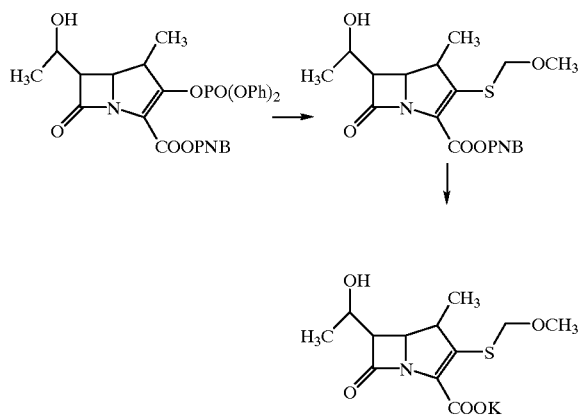

To a solution of p-nitrobenzyl (4R,5R,6S)-3-(diphenyloxyphosphinoyloxy)-6-((1'R)-hydroxyethyl)-4-methyl-7-oxo-1-azabicyclo[3.2.0]hept-2-ene-2-carboxylate (892 mg, 1.5 mmol) in dry dimethyl formamide (15 ml), at −50° C., a solution of methoxymethanethiol (152 mg, 1.95 mmol) in $CDCl_3$ (3 ml) and subsequently diisopropylethylamine (334μl, 1.95 mmol) was added. The reaction mixture was allowed to reach 0° C. After 2 hr at 0° C., the reaction mixture was diluted with ethyl acetate (300 ml) and the solution left at room temperature for 5 min.

This solution was washed subsequently with 10% aqueous $K_2CO_3$ solution (125 ml), three portions of water (100 ml each) and with brine (100 ml). The organic layer was dried over magnesium sulfate and the solvent removed in vacuo. The residue was chromatographed on silica gel (50 g, 63–200 μm) using toluene ethyl acetate (2:1) and (1:1) to give the title compound as a pale yellow non-crystalline solid (yield 78 %). IR spectrum in $CH_2Cl_2$: 3600, 3050, 2900, 1770, 1710, 1605, 1520, 1345, 1210, 1135, 1080 $cm^{-1}$.

Potassium (4R,5S,6S)-6-((1'R)-hydroxyethyl)-3-(methoxymethylthio)-4-methyl-7-oxo-1- azabicyclo[3.2.0] hept-2-ene-2-carboxylate To 10% palladium on carbon (750 mg), prehydrogenated at 0° C. in a two phase mixture of ethyl acetate (30 ml) and $KHCO_3$ (85 mg, 0.85 mmol) in water (12 ml) a solution of p-nitrobenzyl (4R,5S,6S)-6-((1'R)-hydroxyethyl)-3-(methoxymethylthio)-4- methyl-7-oxo-1-azabicyclo[3.2.0]hept-2-ene-2-carboxylate (479 mg, 1.13 mmol) in ethyl acetate (10 ml) was added by a syringe. The mixture was then hydrogenated at ambient pressure and 0° C. After 70, min the uptake of hydrogen (70 ml) became very slow. Additional catalyst (150 mg) was added and hydrogenation was continued for additional 100 min. Additional hydrogen (50 ml) was consumed. The catalyst was removed by filtration, washed with ethyl acetate (5 ml) and water (2 ml) and the filtrate transferred to a separatory funnel. The aqueous layer was collected and the organic layer extracted with a solution of $KHCO_3$ (28 mg, 0.28 mmol) in water (3 ml). The combined aqueous solutions were evacuated in order to remove residual ethyl acetate and then lyophilized at −30° C in high vacuo (0.0013 mbar) (0.001 mm) to give the pure tiltle compound as white powder (yield 50%). UV-spectrum in water $\lambda_{max}$=292 nm (ε=8000). NMR spectrum in $D_2O$ (int. standard $Me_3SiCD_2CD_2COONa$): 1.21 (d, 3H, J=7 Hz), 1.31 (d, 3H, J=6 Hz), 3.43 (s, 3H), 3.45 (m, 1H), 3.52 (m, 1H), 4.2–4.3 (m, 2H), 4.76 and 5.03 (ABq, J=8 Hz, S—$CH_2$—O) ppm.

EXAMPLE 8

(4R,5S,6S)-3-((2-Aminoethoxy)methylthio)-((1'R)-hydroxyethyl)-4-methyl-7-oxo-1- azabicyclo[3.2.0]heit-2-ene-2-carboxylic acid (Ib)

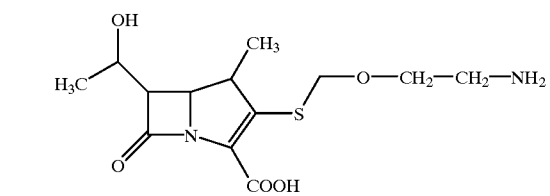

p-Nitrobenzyl (4R,5S,6S)-3-((2-azidoethoxy)methylthio)-6-((1'R)-hydroxyethyl)-4- methyl-7-oxo-1-azabicyclo[3.2.0]hept-2-ene-2-carboxylate According to the procedure described in Example 7, using (2-azidoethoxy)methane-thiol, the title p-nitrobenzyl ester was prepared in 80% yield as a pale yellow non-crystalline solid after chromatography with toluene-ethyl acetate (1:1). IR spectrum in $CH_2Cl_2$: 3600, 3050, 2900, 2100 ($N_3$), 1770, 1710, 1610, 1520, 1350, 1210, 1140, 1085 $cm^-$.

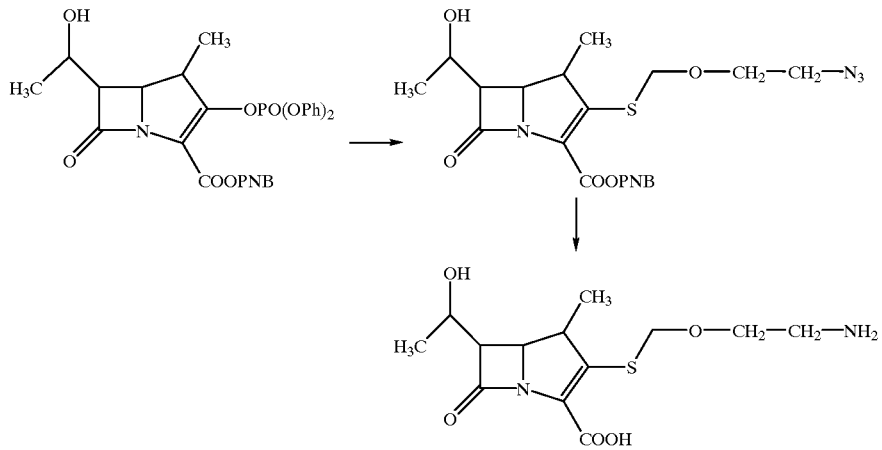

4R,5S,6S)-3-((2-Aminoethoxy)methylthio)-6-((1'R)-hydroxyethyl)-4-methyl-7-oxo-1- azabicyclo[3.2.0]hept-2-ene-2-carboxylic acid (zwitterionic form)

10% Palladium on carbon (700 mg) was prehydrogenated at 0° C. in a two phase mixture of ethyl acetate (30 ml) and water (15 ml) and a solution of p-nitrobenzyl (4R,5S,6S)-3-((2-azidoethoxy)methylthio)-6-((1'R)-hydroxyethyl)-4-methyl-7-oxo-1- azabicyclo[3.2.0]hept-2-ene-2-carboxylate (422 mg, 0.884 mmol) in ethyl acetate (10 ml) was added by a syringe at 0° C. After 65 min of hydrogenolysis at 0° C. and ambient pressure, the uptake of hydrogen (70 ml) became slow. Additional catalyst (100 mg) was added and hydrogenation continued at 0° C. for additional 75 min. Additional hydrogen (35 ml) was absorbed. The catalyst was removed by filtration, washed with ethyl acetate (5 ml) and water (3 ml) and the filtrate transferred to a separatory funnel. The aqueous layer was collected and the organic layer extracted with cold water (3 ml). The combined aqueous solutions were evacuated in order to remove residual ethyl acetate and then lyophilized at −30° C in high vacuo (0.0013 mbar) (0.001 mm) to give the title compound as a white powder in 68% yield. UV-spectrum in water:

$\lambda_{max}$ 292 nm ($\epsilon$=8000). NMR spectrum in D$_2$O (internal standard Me$_3$SiCD$_2$CD$_2$COONa): 1.21 (d, 3H, J=7 Hz), 1.30 (d, 3H, J=6 Hz), 3,23 (m, 2H), 3.48 (dd, 1H), 3.55 (m, 1H) 3.70 and 3.93 (2m, 2H), 4.26 (complex signal, 2H), 4.78 and 5.17 (ABq, 2H, J=11 Hz, S—CH$_2$—O) ppm.

EXAMPLE 9
(4R,5S,6S)-3-((2-(Formimidoylamino)ethoxy)methylthio)-((1'R)-hydroxyethyl)-4-methyl-7-oxo-1-azabicyclo[3.2.0]hept-2-ene-2-carboxylic acid (Ic) (zwitterionic form)

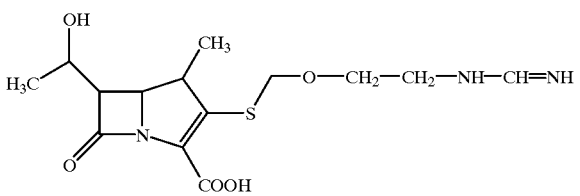

To a solution of (4R,5S,6S)-3-((2-aminoethoxy)methylthio)-((1'R)-hydroxyethyl)-4- methyl-7-oxo-1-azabicyclo[3.2.0]hept-2-ene-2-carboxylic acid (4.7 mg, 13.8 μmol) in water (0.18 ml) at 0° C. a 0.5 N solution of KHCO$_3$ (83 μl, 41 μmol) and subsequently solid ethyl formimidate hydrochloride (4.5 mg, 41 μmol) was added. After 30 min at 0 ° C., additional 0.5 N KHCO$_3$ (55 μl, 28 μmol) and ethyl formimidate hydrochloride (3.0 mg, 28 μmol) were added (pH=8) and the reaction mixture stirred at 0° C. for 60 min. Finally, a 0.5 M solution of potassium carbonate (9 μl, 45 μmol) was added and the mixture stirred for 30 min at 0° C.

The soution was purified at 0° C. by passing slowly through a ion exchange column containing Dowex 50W×4 (0.5 g, Na$^+$-cycle) using water as an eluent. 12 Fractions (0.5 ml) were taken and investigated by TLC (reversed phase silica gel RP-18, water-acetonitrile (3:1). The product containing fractions were combined and the acetonitrile removed by evaporation in high vacuum. The resulting aqueous solution was lyophilized at 0.0013 mbar (0.001 mm) to give the title compound in 31% yield as a colourless amorphous solid. UV spectrum in water:

$\lambda_{max}$=292 nm ($\epsilon$=8000). NMR spectrum in D$_2$O (internal standard Me$_3$SiCD$_2$CD$_2$COONa): 1.21 (d, 3H, J=7 Hz), 1.30 (d, 3H, J=6 Hz), 3,4–4.0 (m, 6H), 4.2–4.3 (m, 2H), 4.71 and 5.17 (ABq, 2H, J=7 Hz), 7.8 (d, 1H, J=3 Hz).

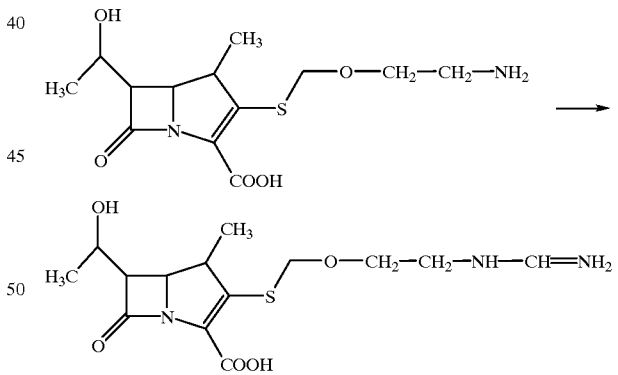

EXAMPLE 10
(4R,5S,6S)-3-((2-Amino-1,1-dimethylethoxy)methylthio)-((1'R)-hydroxyethyl)-4-methyl-7-oxo-1-azabicyclo[3.2.0]hept-2-ene-2-carboxylic acid (Id)

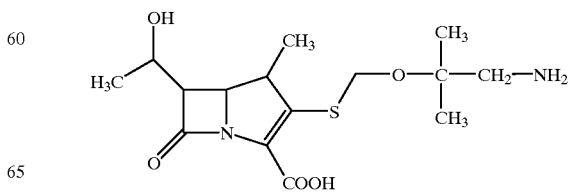

p-Nitrobenzyl (4R,5S,6S)-3-((2-azido-1,1-dimethylethoxy)methylthio)-6-((1'R)-hydroxyethyl)-4-methyl-7-oxo-1-azabicyclo[3.2.0]-hept-2-ene-2-carboxylate According to the procedure described in Example 7, using (2-azido-1,1- dimethylethoxy)methanethiol, the title p-nitrobenzyl ester was prepared in 72% yield as a pale yellow non-crystalline solid after chromatography with toluene-ethyl acetate (2:1). IR spectrum in $CH_2Cl_2$: 3600, 3025, 2990, 2105 ($N_3$), 1775, 1710, 1610, 1525, 1350, 1210, 1135, 1055 $cm^{-1}$.

EXAMPLE 11
Sodium or potassium (4R,5S,6S)-3-(acetamidomethylthio)-((1'R)-hydroxyethyl)-4- methyl-7-oxo-1-azabicvclo[3.2.0] hept-2-ene-2-carboxylate (Ie)

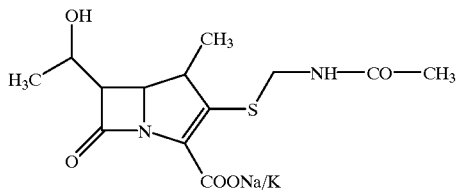

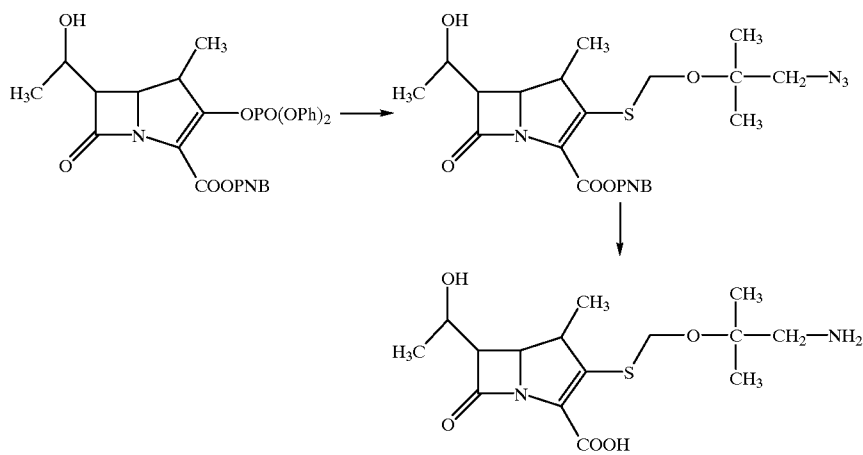

(4R,5S,6S)-3-((2-amino-1,1-dimethylethoxy)methylthio)-6-((1'R)-hydroxyethyl)-4- methyl-7-oxo-1-azabicyclo[3.2.0] hept-2-ene-2-carboxylic acid (zwitterionic form)

According to the procedure described in Example 8, the title compound was prepared in 28% yield as a colourless lyophilized powder by hydrogenolysis of p-nitrobenzyl (4R,5S,6S)-3-((2-azido-1,1-dimethyl-ethoxy)methylthio)-6-((1R)-hydroxyethyl)-4-methyl-7-oxo-1-azabicyclo[3.2.0]-hept-2-ene-2-carboxylate. UV spectrum in $H_2O$: $\lambda_{max}$=292 nm (s=8000).

p-Nitrobenzyl (4R,5S,6S)-3-(acetamidomethylthio)-6-((1'R)-hydroxyethyl)-4-methyl-7- oxo-1-azabicyclo[3.2.0] hept-2-ene-2-carboxylate According to the procedure described in Example 7, using N-(mercaptomethyl)-acetamide, the title p-nitrobenzyl ester was prepared in 36% yield as a pale yellow non-crystalline solid after chromatography with ethyl acetate. IR spectrum in $CH_2Cl_2$: 3600 (OH), 3430 (NH), 3050, 2950, 1770 (β-lact C=O), 1705 (ester C=O) 1675 (amide I), 1605, 1525 ($NO_2$), 1505 (amide II), 1350($NO_2$), 1210, 1135 $cm^{-1}$.

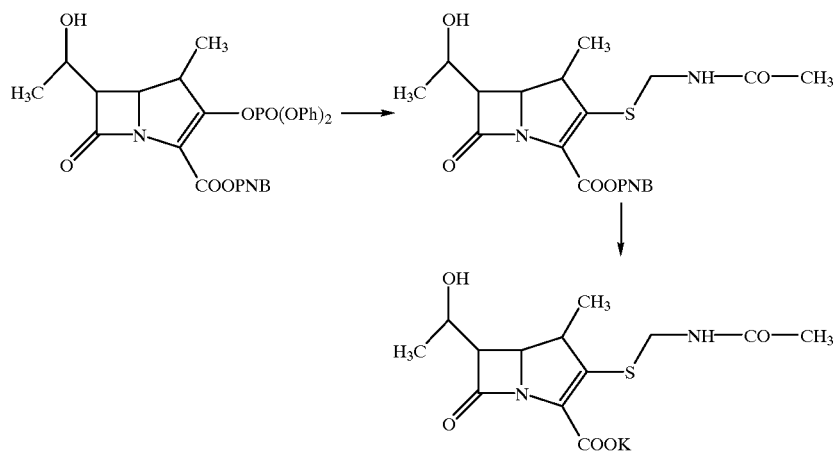

Potassium (4R,5S,6S)-3-(acetamidomethylthio)-((1'R)-hydroxyethyl)-4-methyl-7-oxo-1-azabicyclo[3.2.0]hept-2-ene-2-carboxylate According to the procedure described in Example 7 the p-nitrobenzyl ester was hydrogenolyzed to give the title compound as a white powder in 54% yield after lyophilisation. UV-spectrum in water: $\lambda_{max}$ 294 nm ($\epsilon$=8000). NMR-spectrum in D$_2$O (internal standard Me$_3$CD$_2$CD$_2$COONa): 1.31 (d, 3H, J=7 Hz), 1.30 (d, 3H, J=6 Hz), 2.01 (s, 3H), 3.42–3.48 (2m, 2H), 4.20–4.25 (2m, 2H), 4.36 and 4.66 (ABq, 2H, J=14 Hz, S—CH$_2$—N) ppm.

EXAMPLE 12
(4R,5S,6S)-3-((2-Aminoacetamido)methylthio)-6-((1'R)-hydroxyethyl)-4-methyl-7-oxo-1-azabicyclo[3.2.0]hept-2-ene-2-carboxylic acid (If)

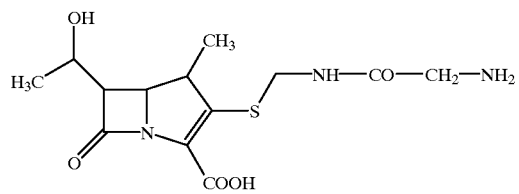

p-Nitrobenzyl (4R,5S,6S)-3-((2-azidoacetamido)methylthio)-6-((1'R)-hydroxyethyl)-4-methyl-7-oxo-1-azabicyclo[3.2.0]hept-2-ene-2-carboxylate According to the procedure described in Example 7, using 2-azido-N-(mercaptomethyl)-acetamide the title p-nitrobenzyl ester was prepared as a pale yellow non-crystalline solid after chromatography with toluene-ethyl acetate (1:1) and ethyl acetate in 63% yield. IR-spectrum in CH$_2$Cl$_2$: 3600 (OH), 2900 (NH), 2100 (N$_3$), 1770 (β-lactam C=O), 1705 and 1695 (ester and amide I), 1600 (C=C), 1520 (NO$_2$ and amide II), 1350 NO$_2$, 1205, 1130 cm$^{-1}$.

sation. UV-spectrum in water: $\lambda_{max}$ 292 nm ($\epsilon$=8000). NMR spectrum in D$_2$O (internal standard Me$_3$CD$_2$CD$_2$COONa): 1.21 (d, 3H, J=7 Hz), 1.30 (d, 3H, J=6 Hz), 3.5 (complex signal, 2H), 3.77 (s, 2H), 4.25 (complex signal, 2H), 4.41 and 4.72 (ABq, 2H, J=14 Hz, S—CH$_2$—N) ppm.

EXAMPLE 13
Sodium or potassium (4R,5S,6S)-3-((2,3-dioxo-4-ethyl-piperazinyl)methylthio)-6-((1'R)-hydroxyethyl)-4-methyl-7-oxo-1-azabicyclo[3.2.0]hept-2-ene-2-carboxylate (Ig)

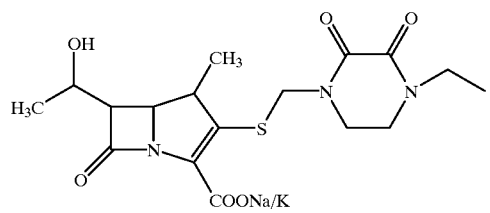

p-Nitrobenzyl (4R,5S,6S)-3-((2,3-dioxo-4-ethyl-piperazinyl)methylthio)-6-((1'R)-hydroxyethyl)-4-methyl-7-oxo-1-azabicyclo[3.2.0]hept-2-ene-2-carboxylate To a solution of p-nitrobenzyl (4R,5R,6S)-3-(diphenyloxyphosphinoyloxy)-6-((1'R)-hydroxyethyl)-4-methyl-7-oxo-1-azabicyclo[3.2.0]hept-2-ene-2-carboxylate (118 mg, 0.2 mmol) in dry dimethyl formamide (1.5 ml), at −50° C., a solution of 1-ethyl-4-(mercaptomethyl)-piperazine-2,3-dione (49 mg, 0.26 mmol) in CDCl$_3$ (1.2 ml) and subsequently diisopropylethylamine (44 μl, 0.26 mmol) were added. The reaction mixture was allowed to reach 0° C. After 3 hr at 0° C., the reaction mixture was diluted with ethyl acetate (50 ml) and the solution left at room temperature for 5 min. This solution was washed subsequently with 10% aqueous K$_2$CO$_3$ solution (20 ml) and with brine (20 ml). The organic layer was dried over magnesium sulfate

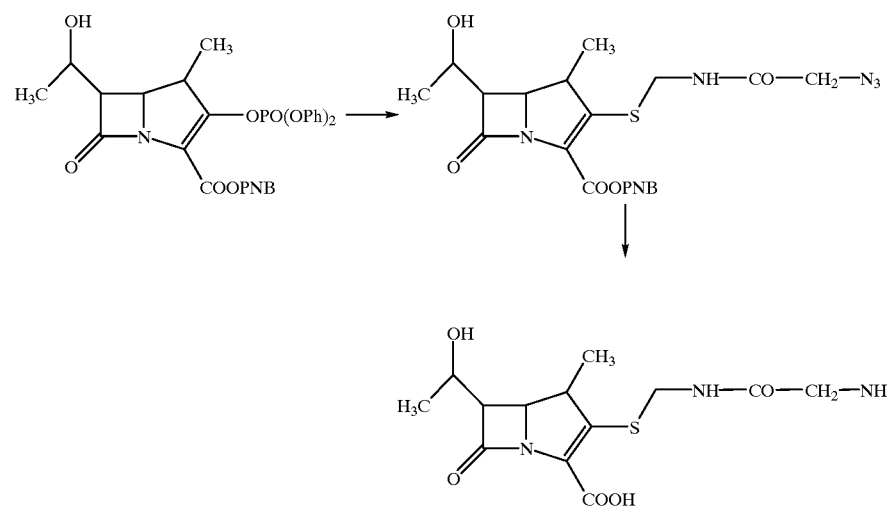

(4R,5S,6S)-3-((2-Aminoacetamido)methylthio-6-((1'R)-hydroxyethyl)-4-methyl-7-oxo-1-azabicyclo[3.2.0]hept-2-ene-2-carboxylic acid (zwitterionic form)

According to the procedure described in Example 8 the p-nitrobenzyl ester was hydrogenolyzed to give the title compound as a white powder in 53% yield after lyophiliand the solvent removed in vacuo. The residue was chromatographed on silica gel (4 g, 63–200 μm) using chloroform-methanol (9:1) to give the title p-nitrobenzyl ester as a pale yellow non-crystalline solid (yield 89%). IR spectrum in CH$_2$Cl$_2$: 3600, 3050, 2900, 1770, 1710 (shoulder), 1685, 1605, 1520, 1345, 1200, 1135 cm$^{-1}$.

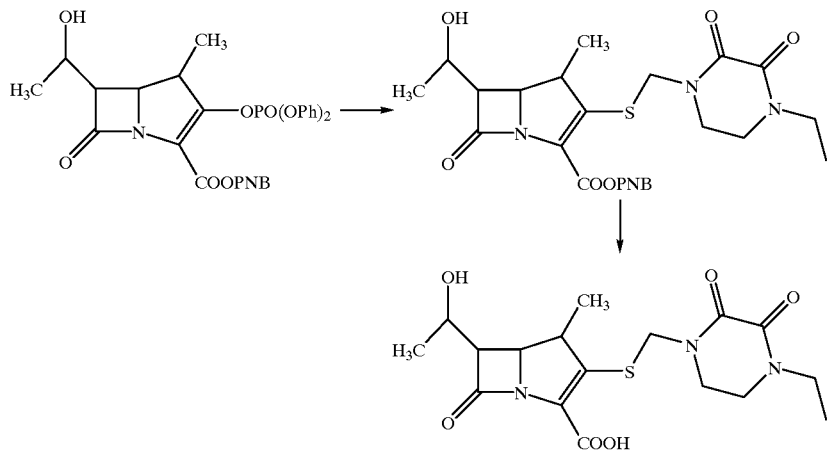

Potassium (4R,5S,6S)-3-((2,3-dioxo-4-ethyl-piperazinyl) methylthio)-6-((1'R)-hydroxyethyl)-4-methyl-7-oxo-1-azabicyclo[3.2.0]hept-2-ene-2-carboxylate To 10% palladium on carbon (90 mg), prehydrogenated at 0° C. in a two phase mixture of ethyl acetate (4 ml) and $KHCO_3$ (10.6 mg, 0.106 mmol) in water (3 ml) a solution of p-nitrobenzyl (4R,5S,6S)-3-((2,3-dioxo-4-ethyl-piperazinyl)methylthio) -6- ((1'R)-hydroxyethyl)-4-methyl-7-oxo-1-azabicyclo(3.2.0)hept-2-ene-2-carboxylate (76 mg, 0.14 mmol) in ethyl acetate (4 ml) was added by a syringe. The mixture was then hydrogenated at ambient pressure and 0° C. After 70 min the uptake of hydrogen (10.8 ml) became very slow. Additional catalyst (30 mg) was added and hydrogenation was continued for additional 45 min. Additional hydrogen (6.6 ml) was consumed. The catalyst was removed by filtration, washed with ethyl acetate (2 ml) and water (1 ml) and the filtrate tranferred to a separatory funnel. The aqueous layer was collected and the organic layer extracted with a solution of $KHCO_3$ (3.6 mg, 0.036 mmol) in water (1 ml). The combined aqueous solutions were evacuated in order to remove residual ethyl acetate and then lyophilized at −30° C. in hygh vacuo (0.0013 mbar) (0.001 mm) to give the pure tiltle compound as white powder (yield 65%). UV-spectrum in water $\lambda_{max}$=292 nm ($\delta$=8000), 222 nm ($\epsilon$=11200). NMR spectrum in $D_2O$ (int. standard $Me_3CD_2CD_2COONa$): 1.1–1.3 (m, 6H), 1.30 (d, 3H, J=6 Hz), 3.50 (m, 6H), 3.4–3.8 (m, 8H), 4.18 (m, 1H), 4.25 (m, 1H), 4.30 and 5.30 (ABq, 2H, J=14 Hz, N—$CH_2$—S) ppm.

EXAMPLE 14

Biological Activity

1. In Vitro Antibacterial Activity

Table I shows inhibition diameters in mm after investigation of 10 μg of the representative antibiotics (plate test results). The tests were carried out in sterile polypropylene dishes (diameter 8.5 cm) containing 10 ml of Difco Nutrient Agar. Inhibition was recorded after 18 hrs at 37° C. (inoculum ca. $10^{-5}$ cells).

TABLE I

|  | Ib | Ic | Ie | If |
|---|---|---|---|---|
| Staph. aureus DSM 1104 | 39 | 39 | 36 | 33 |
| Staph. aureus resistant | 35 | 35 | 32 | 30 |
| Staph. aureus 25768 | 28 | 26 | 27 | 25 |

TABLE I-continued

|  | Ib | Ic | Ie | If |
|---|---|---|---|---|
| Staph. aureus Innsbruck | 9 | 8 | — | 12 |
| Escherichia coli DSM 1103 | 30 | 30 | 32 | 27 |
| Escherichia coli TEM 1 | 33 | 33 | 34 | 33 |
| Enterobacter cloacae DSM 30054 | 26 | 25 | 27 | 23 |
| Enterococcus | 21 | 21 | 18 | 20 |
| Pseudomonas aer. DSM 1117 | 27 | 25 | 16 | 18 |
| Pseudomonas aer. resistant | 17 | 13 | — | 14 |

2. β-Lactamase Inhibition Activity Against Isolated (Cell Free) Enzymes

Table II shows the β-lactamase inhibition activity (mol per liter) of the representative compounds according to the invention as determined by the nitrocefin method. $IC_{50}$ values were determined in a 1 cm UV cell at 37° C. after a 15 min preincubation period of enzyme and the inhibitor.

TABLE II

| | $IC_{50}$ (mol per liter) | |
|---|---|---|
| compound | Penicillinase from E. coli TEM 1 | β-Lactamase from Enterobacter cloacae |
| Ia | $2 \times 10^{-7}$ | $4 \times 10^{-9}$ |
| Ib | $5.5 \times 10^{-7}$ | $8.5 \times 10^{-9}$ |
| Ie | $3 \times 10^{-7}$ | $6 \times 10^{-9}$ |

3. β-Lactamase Inhibition Activity Against Resistant Bacteria

Table III shows the antibacterial activity (MIC, μg per ml) of ceftazidime (CAZ) without and in combination with representative compound Ia (potassium salt).

TABLE III

| bacterial strain | enzyme | CAZ (μg per ml) | CAZ + Ia (μg per ml) |
|---|---|---|---|
| E. cloacae EB 131 | Type 1 Ceph'ase | >64 | 2 + 1 |
| K. pneumoniae KL 140 | CAZ-ase | >64 | 2 + 1 |
| K. pneumoniae KL 141 | CAZ-ase | >64 | 64 + 0.12 |
| E. coli EC 227 | CAZ-ase | >64 | 0.25 + 0.5 |
| E. coli EC 228 | CAZ-ase | 16 | 1 + 0.5 |
| E. coli EC 225 | TEM-5 | 64 | 2 + 0.5 |

4. Stability in Phosphate Buffer

Table IV shows the half-lives of hydrolysis (in hrs) of the representative compounds in physiological phoshate buffer pH 7.4 and 37° C. as determined by the UV method.

TABLE IV

| compound | half-life (hrs) |
|---|---|
| Ia | 50 |
| Ib | 50 |
| Ic | 35 |
| Id | 50 |
| Ie | 40 |
| If | 16 |
| Ig | 42 |

5. Oral Activity

Table V shows the plasma level and half-life in mice after oral application of compound Ia (potassium salt) according to the invention (dose 25 mg per kg).

TABLE V

| compound | Plasma level ($\mu$g per ml) 10 min after application | Approximative serum half-life (min) |
|---|---|---|
| Ia | 5.6 | 25 |

6. Cytotoxicity

Table VI shows the cytotoxicity in *Sacharomyces cerevisiae* of the representative compounds (1.0 mg) as determined by the agar diffusion method. Sterile PP dishes of 8.5 cm diameter containing 10 ml of yeast and mold agar were used. Cytotoxicity was recorded after a 16 hrs incubation period at 30° C. (inoculum approx. $10^5$ cells).

TABLE VI

| compound | inhibition diameter (mm) |
|---|---|
| Ib | 0 |
| Ie | 0 |
| If | 0 |

EXAMPLE 15

Production of Pharmaceutical Preparations

A unit dose form is prepared by mixing 60 mg of (4R,5S,6S)-3- ((2-aminoethoxy)methylthio)-((1'R)-hydroxyethyl)-4-methyl-7-oxo-1- azabicyclo[3.2.0]hept-2-ene-2-carboxylic acid (Ib) with 20 mg of lactose and 5 mg of magnesium stearate and the 85 mg of mixture are added to a No. 3 gelatin capsule. Similarly, if more active constituents and less lactose are used, other dose forms may be prepared and filled into No. 3 gelatin capsules. Similarly, larger gelatin capsules and also compressed tablets and pills may also be produced. The following examples illustrate the production of pharmaceutical preparations.

| Tablet (for oral application) | |
|---|---|
| (4R,5S,6S)-3-((2-Aminoethoxy)methylthio)-((1'R)-hydroxyethyl)-4-methyl-7-oxo-1-azabicyclo[3.2.0]hept-2-ene-2-carboxylic acid (Ib) | 120 mg |
| Corn starch | 6 mg |
| Magnesium stearate | 232 mg |
| Dicalcium phosphate | 192 mg |
| Lactose | 250 mg |

The active constituent is mixed with the dicalcium phosphate, lactose and about half of the corn starch and coarse-sieved. It is dried in high vacuum and again sieved through sieves having mesh widths of 1.00 mm (No.16 screens). The rest of the corn starch and the magnesium stearate is added and the mixture is pressed to give tablets which each weight 800 mg and have a diameter of about 1.27 cm (0.5 in.).

Parenteral Solution

| Ampoule | |
|---|---|
| (4R,5S,6S)-3-((2-Aminoethoxy)methylthio)-((1'R)-hydroxyethyl)-4-methyl-7-oxo-1-azabicyclo[3.2.0]hept-2-ene-2-carboxylic acid (Ib) | 250 mg |
| Sterile water (is added from a separate ampoule using a syringe immediately before use) | 4 ml |

| Ophtalmic solution | |
|---|---|
| (4R,5S,6S)-3-((2-Aminoethoxy)methylthio)-((1'R)-hydroxyethyl)-4-methyl-7-oxo-1-azabicyclo[3.2.0]hept-2-ene-2-carboxylic acid (Ib) | 50 mg |
| Hydroxypropylmethylcellulose | 5 mg |
| Sterile water (is added from a separate ampoule using a syringe immediately before use) | 1 ml |

| Otic solution | |
|---|---|
| (4R,5S,6S)-3-((2-Aminoethoxy)methylthio)-((1'R)-hydroxyethyl)-4-methyl-7-oxo-1-azabicyclo[3.2.0]hept-2-ene-2-carboxylic acid (Ib) | 50 mg |
| Benzalkonium chloride | 0.1 mg |
| Sterile water (is added from a separate ampoule using a syringe immediately before use) | 1 ml |

| Topical cream or ointment | |
|---|---|
| (4R,5S,6S)-3-((2-Aminoethoxy)methylthio)-((1'R)-hydroxyethyl)-4-methyl-7-oxo-1-azabicyclo[3.2.0]hept-2-ene-2-carboxylic acid (Ib) | 100 mg |
| Polyethylene glycol 4000 | 400 mg |
| Polyethylene glycol 400 | 1.0 g |

The active component in the above preparations can be mixed alone or together with other biologically active components, for example with other antibacterial agents such as a penicillin or cephalosporins or with other therapeutic agents, such as probenicid.

It is understood that the specification and examples are illustrative but not limitative of the present invention and that other embodiments within the scope of ithe invention will suggest themselves to those skilled in the art.

What is claimed:

1. Compounds of the structural formula I

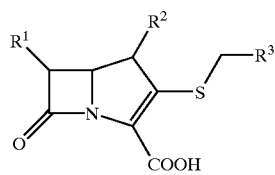

and their pharmaceutically acceptable salts, esters and amide derivatives, in which $R^1$ denotes hydrogen, hydroxymethyl or 1-hydroxyethyl, $R^2$ denotes hydrogen or methyl and $R^3$ denotes a pharmaceutically acceptable group which is bonded to the remaining part of the molecule by an oxygen-carbon single bond or a nitrogen-carbon single bond and which is selected from the group consisting of substituted or unsubstituted: alkoxy, alkenyloxy, alkinyloxy, cycloalkoxy, N-heterocyclyl, heterocyclyloxy, heterocyclylcarbonyloxy, heterocyclylthiocarbonyloxy, acyloxy, thioacyloxy, alkoxycarbonyloxy, carbamoyloxy, thiocarbamoyloxy, heterocyclyloxycarbonyloxy, heterocyclyloxythiocarbonyloxy, N-heterocyclylcarbamoyloxy, N-heterocyclylthiocarbamoyloxy, heterocyclylcarbonylamino, heterocyclyithiocarbonylamino, heterocyclyloxycarbonylamino, acylamino, alkoxycarbonylamino, alkoxythiocarbonylamino, thioacylamino, N-heterocyclylcarbamoylamino, N-heterocyclylthiocarbamoylamino, carbamoylamino, thiocarbamoylamino, imidoylamino, guanidino, N-heterocyclyl-alkoxycarbonylamino, N-heterocyclyl-alkylthiocarbonylamino and N-sulfonylamino where the foregoing alkyl, alkenyl, alkinyl, acyl, thioacyl or imidoyl molecule parts contain 1 to 6 carbon atoms and the heterocyclyl moiety is monocyclic or bicyclic and contains 3 to 10 ring atoms, of which one or more are selected from the series consisting of: oxygen, sulphur and nitrogen and where the substituents of the above-mentioned groups $R^3$ may be: alkyl, acyl, thioacyl, heterocyclyl, hydroxyl, hydroxyalkyl, alkoxy, hydroxyalkoxy, aminoalkoxy, amidinoalkoxy, guanidinoalkoxy, acyloxy, heterocyclyloxy, alkyiheterocyclyloxy, hydroxyalkylheterocyclyloxy, aminoalkyiheterocyclyloxy, carbamoyl, alkylcarbamoyl, dialkylcarbamoyl, carbamoyloxy, alkylcarbamoyloxy, dialkylcarbamoyloxy, thiocarbamoyl, alkylthiocarbamoyl, dialkylthiocarbamoyl, thiocarbamoyloxy, alkylthiocarbamoyloxy, dialkyithiocarbamoyloxy, mercapto, alkylthio, hydroxyalkylthio, aminoalkylthio, monoalkylaminoalkylthio, dialkylaminoalkylthio, amidinoalkylthio, acylthio, heterocyclylthio, alkylheterocyclylthio, hydroxyalkylheterocyclylthio, aminoalkylheterocyclylthio, carbamoylthio, monoalkylcarbamoylthio, dialkylcarbamoylthio, thiocarbamoylthio, alkylthiocarbamoylthio, dialkylcarbamoylthio, amino, monoalkylamino, hydroxyalkylamino, aminoalkylamino, dialkylamino, oxo, oximino, or alkylimino, imidoylamino, alkylimidoylamino, dialkylimidoylamino, trialkylammonium, cycloalkylamino, heterocyclylamino, alkylheterocyclylamino, heterocyclylcarbonylamino, alkylheterocyclylcarbonylamino, acylamino, amidino, monoalkylamidino, dialkylamidino, guanidino, alkylguanidino, dialkylguanidino, carbamoylamino, thiocarbamoylamino, alkylcarbamoylamino, thiocarbamoylamino, alkylthiocarbamoylamino, nitro, chloro, bromo, fluoro, iodo, azido, cyano, alkylsulphinyl, alkylsulphonyl, sulphonamido, sulphamoyloxy, alkylsulphamoyloxy, alkylsulphonyloxy or suipho, sulphoxy, carboxamido, N-monoalkylcarboxamido, N,N-dialkylcarboxamido or carboxy, where the substituents, independently of one another, occur once or several times and their alkyl moiety contains 1 to 6 carbon atoms, and where the heterocyclic moiety is monocyclic or bicyclic and contains 3 to 10 ring atoms, of which one or more are selected from the series comprising: oxygen, sulphur and nitrogen.

2. Compounds according to claim 1, characterized in that $R^1$ denotes hydrogen, hydroxymethyl or 1-hydroxyethyl, $R^2$ denotes hydrogen or methyl and $R^3$ is selected from the group consisting of substituted or unsubstituted alkoxy, heterocyclyloxy, acyloxy, carbamoyloxy, N-heterocyclyl, acylamino, carbamoylamino, imidoylamino where the foregoing alkyl, acyl, thioacyl, or imidoyl molecule parts contain 1 to 3 carbon atoms and the heterocyclyl moiety is monocyclic and contains 3 to 6 ring atoms, of which one or more are selected from the series consisting of: oxygen, sulphur and nitrogen and where the substituents of the above-mentioned groups $R^3$ may be: alkyl, acyl, thioacyl, heterocyclyl, hydroxyl, hydroxyalkyl, alkoxy, hydroxyalkoxy, aminoalkoxy, amidinoalkoxy, guanidinoalkoxy, acyloxy, heterocyclyloxy, alkylheterocyclyloxy, hydroxyalkylheterocyclyloxy, aminoalkylheterocyclyloxy, carbamoyl, alkylcarbamoyl, dialkylcarbamoyl, carbamoyloxy, alkylcarbamoyloxy, dialkylcarbamoyloxy,thiocarbamoyl, alkylthiocarbamoyl, dialkyithiocarbamoyl, thiocarbamoyloxy, alkylthiocarbamoyloxy, dialkylthiocarbamoyloxy, mercapto, alkylthio, hydroxyalkylthio, aminoalkylthio, monoalkylaminoalkylthio, dialkylaminoalkylthio, amidinoalkylthio, acylthio, heterocyclylthio, alkylheterocyclylthio, hydroxyalkylheterocyclylthio, aminoalkylheterocyclylthio, carbamoylthio, monoalkylcarbamoylthio, dialkylcarbamoylthio, thiocarbamoylthio, alkylthiocarbamoylthio, dialkylcarbamoylthio, amino, monoalkylamino, hydroxyalkylamino, aminoalkylamino, dialkylamino, oxo, oximino, or alkylimino, imidoylamino, alkylimidoylamino, dialkylimidoylamino, trialkylammonium, cycloalkylamino, heterocyclylamino, alkylheterocyclylamino, heterocyclylcarbonylamino, alkyiheterocyclylcarbonylamino, acylamino, amidino, monoalkylamidino, dialkylamidino, guanidino, alkylguanidino, dialkylguanidino, carbamoylamino, thiocarbamoylamino, alkylcarbamoylamino, thiocarbamoylamino, alkylthiocarbamoylamino, nitro, chloro, bromo, fluoro, iodo, azido, cyano, alkylsulphinyl, alkylsulphonyl, sulphonamido, sulphamoyloxy, alkylsulphamoyloxy, alkylsuiphonyloxy or sulpho, sulphoxy, carboxamido, N-monoalkylcarboxamido, N,N-dialkylcarboxamido or carboxy, where the substituents, independently of one another, occur once or several times and their alkyl moiety contains 1 to 6 carbon atoms, and where the heterocyclic moiety is monocyclic and contains 3 to 6 ring atoms, of which one or more are selected from the series consisting of: oxygen, sulphur and nitrogen.

3. Compounds according to claim 1, characterized in that $R^1$ denotes hydrogen, hydroxymethyl or 1-hydroxyethyl, $R^2$ denotes hydrogen or methyl and $R^3$ is selected from the group consisting of: substituted alkoxy, acylamino, N-heterocyclyl and imidoylamino, where the foregoing alkyl, acyl or imidoyl molecule parts contain 1 to 3 carbon atoms and the heterocyclyl moiety is monocyclic and contain 3 to 6 ring atoms, of which one or more are selected from the series consisting of: oxygen, sulphur and nitrogen and where the substituents of the above-mentioned groups $R^3$ are basic groups such as amino, alkylamino, dialkylamino, imidoylamino, amidino and guanidino, in which the alkyl, amidino and imidoyl parts contains 1 to 3 carbon atoms.

4. Compounds according to claim 1, characterized in that $R^1$ denotes 1-hydroxyethyl, $R^2$ denotes methyl and $R^3$ is selected from the group consisting of

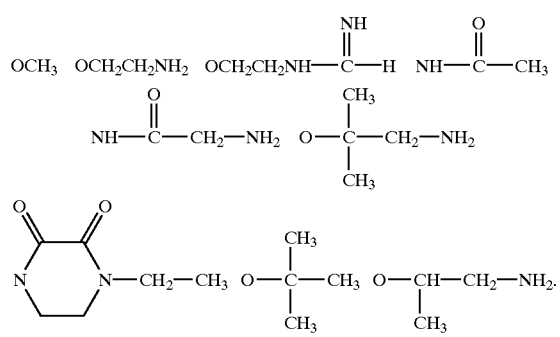

5. A pharmaceutical composition comprising an antibacterial effective amount of at least one compound of claim 1 and a pharmaceutically acceptable carrier or diluent.

6. A process for preparing the composition of claim 5, which comprises incorporating an antibacterial effective amount of at least one compound of claim 1 into a pharmaceutically acceptable carrier or diluent.

7. A process for preparing the compounds of claim 1, which comprises reacting a compound of formula

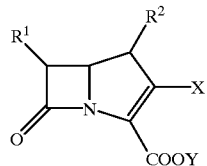

wherein $R^1$ and $R^2$ are as defined in claim 1, X is a leaving group and Y is a carboxy protecting group, with a thiol of formula $$HS-CR_2-R^3$$

or an organic or inorganic salt thereof, wherein $R^3$ is as defined in claim 1.

8. A process for preparing the compounds of claim 1, which comprises reacting with a deprotecting agent a compound of formula

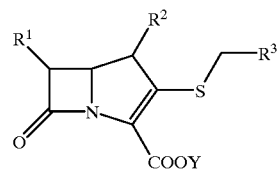

wherein $R^1$, $R^2$ and $R^3$ are as defined in claim 1 and Y is a carboxy protecting group.

* * * * *